(12) United States Patent
Wang et al.

(10) Patent No.: US 10,300,005 B2
(45) Date of Patent: May 28, 2019

(54) PERSONAL CARE COMPOSITION AND METHODS CONTAINING HYDROPHOBICALLY-MODIFIED HYDROXYETHYLCELLULOSE

(75) Inventors: Miao Wang, Schwenksville, PA (US); Emmett M. Partain, Bound Brook, NJ (US)

(73) Assignees: Union Carbide Chemicals & Plastics Technology LLC, Midland, MI (US); Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 14/235,579

(22) PCT Filed: Sep. 14, 2012

(86) PCT No.: PCT/US2012/055380
§ 371 (c)(1),
(2), (4) Date: Jan. 28, 2014

(87) PCT Pub. No.: WO2013/048778
PCT Pub. Date: Apr. 4, 2013

(65) Prior Publication Data
US 2014/0199250 A1    Jul. 17, 2014

Related U.S. Application Data

(60) Provisional application No. 61/540,834, filed on Sep. 29, 2011.

(51) Int. Cl.
| | | |
|---|---|---|
| *A61Q 19/00* | (2006.01) |
| *A61Q 5/00* | (2006.01) |
| *A61Q 5/06* | (2006.01) |
| *A61K 8/73* | (2006.01) |
| *A61K 8/67* | (2006.01) |
| *A61K 8/81* | (2006.01) |

(52) U.S. Cl.
CPC .............. *A61K 8/731* (2013.01); *A61K 8/678* (2013.01); *A61K 8/8152* (2013.01); *A61Q 5/00* (2013.01); *A61Q 5/06* (2013.01); *A61Q 19/00* (2013.01)

(58) Field of Classification Search
None
See application file for complete search history.

(56) References Cited

U.S. PATENT DOCUMENTS

| | | |
|---|---|---|
| 4,228,277 A | 10/1980 | Landoll |
| 4,663,159 A | 5/1987 | Brode, II et al. |
| 4,845,175 A | 7/1989 | Lo |
| 4,859,456 A | 8/1989 | Marschner |
| 5,426,182 A | 6/1995 | Jenkins et al. |
| 5,910,472 A | 6/1999 | Elliott et al. |
| 6,372,901 B1 * | 4/2002 | Partain, III ............. C08B 11/16 536/90 |
| 2006/0051311 A1 | 3/2006 | Walter et al. |
| 2006/0134049 A1 * | 6/2006 | Keenan .................... A61K 8/81 424/70.15 |
| 2008/0178899 A1 * | 7/2008 | Moenks ................. A61K 8/046 132/203 |

FOREIGN PATENT DOCUMENTS

| | | |
|---|---|---|
| EP | 0875557 A2 | 11/1998 |
| EP | 0878189 A2 | 11/1998 |
| EP | 0956850 A1 | 11/1999 |
| WO | 199113138 A1 | 9/1991 |
| WO | 199617916 A1 | 6/1996 |

\* cited by examiner

*Primary Examiner* — Jyothsna A Venkat

(57) ABSTRACT

Described are personal care compositions, comprising water, nonionic cellulose ethers having hydroxyethyl groups and being further substituted with one or more hydrophobic substituents, and at least one hair fixative polymer, moisturizer, conditioner, humectant, cationic conditioning polymer, antioxidant, anti-aging active, or sun care active.

15 Claims, No Drawings

PERSONAL CARE COMPOSITION AND METHODS CONTAINING HYDROPHOBICALLY-MODIFIED HYDROXYETHYLCELLULOSE

CROSS REFERENCE TO RELATED APPLICATIONS

This application is a 35 USC § 371 national phase filing of PCT/US2012/055380 filed Sep. 14, 2012, which claims the benefit of U.S. Application No. 61/540,834, filed Sep. 29, 2011.

FIELD

The present invention relates to personal care compositions.

BACKGROUND

Personal care compositions must be effective at delivering active ingredients (such as sunscreens, moisturizers, styling polymers, conditioning polymers, and others), while still having good aesthetic properties (tactile, visual, and the like). In fact, aesthetic properties are of paramount importance in personal care, because a consumer associates these properties with performance and value.

When it comes to lotions and creams, a light, fluffy, airy texture is highly valued by consumers. As can be appreciated, it is difficult to incorporate the necessary active ingredients and create such a texture, it is more difficult still to maintain such a texture through the variable and sometimes extreme conditions faced by the product during packaging, transporting, and vending before it arrives in the hands of the consumer. Even were a desirable texture obtainable, traditional rheology modifiers, such as ASE (alkali-soluble emulsion), HASE (Hydrophobically modified alkali-soluble emulsion), HEC (Hydroxyethyl Cellulose), starch, clay, or other natural polymers, do not preserve desirable texture upon exposure to high temperature (also known as heat-aging).

Accordingly, it would be desirable to find new materials to impart improved aesthetics to personal care compositions that also provide stability over time and exhibit a reduced degree of thinning.

DETAILED DESCRIPTION

In one embodiment, the present invention provides a personal care composition comprising a water; nonionic cellulose ethers having hydroxyethyl groups and being further substituted with one or more hydrophobic substituents, wherein the cellulose ether has at least one of the properties a), b) or c):
   a) a retained dynamic viscosity, % $\eta_{80/25}$, of at least 30 percent, wherein % $\eta_{80/25}$=[dynamic solution viscosity at 80° C./dynamic solution viscosity at 25° C.]×100, the dynamic solution viscosity at 25° C. and 80° C. being measured as 1% aqueous solution;
   b) a storage modulus of at least 15 Pascals at 25° C. and a retained storage modulus, % $G'_{80/25}$, of at least 12 percent, wherein % $G'_{80/25}$=[storage modulus at 80° C./storage modulus at 25° C.]×100, the storage modulus at 25° C. and 80° C. being measured as a 1% aqueous solution;
   c) a critical association concentration of less than 15 ppm as measured by light-scattering; and
at least one hair fixative polymer, moisturizer, conditioner, humectant, cationic conditioning polymer, antioxidant, anti-aging active, or sun care active.

One aspect of the present invention are nonionic cellulose ethers having hydroxyethyl groups and being further substituted with one or more hydrophobic substituents, wherein the cellulose ether has at least one of the properties a), b) or c):
   a) a retained dynamic viscosity, % $\eta_{80/25}$, of at least 30 percent, wherein % $\eta_{80/25}$=[dynamic solution viscosity at 80° C./dynamic solution viscosity at 25° C.]×100, the dynamic solution viscosity at 25° C. and 80° C. being measured as 1% aqueous solution;
   b) a storage modulus of at least 15 Pascals at 25° C. and a retained storage modulus, % $G'_{80/25}$, of at least 12 percent, wherein % $G'_{80/25}$=[storage modulus at 80° C./storage modulus at 25° C.]×100, the storage modulus at 25° C. and 80° C. being measured as a 1% aqueous solution;
   c) a critical association concentration of less than 15 ppm as measured by light-scattering.

The hydroxyethyl molar substitution EO MS (ethylene oxide molar substitution) of the polymers prepared from hydroxyethyl cellulose is determined either by simple mass gain or using the Morgan modification of the Zeisel method: P. W. Morgan, *Ind. Eng. Chem., Anal. Ed.,* 18, 500-504 (1946). The procedure is also described in ASTM method D-2364 (2007). The EO MS of the nonionic cellulose ether of the present invention generally is from 1 to 5, preferably from 1.5 to 3.5, more preferably from 1.6 to 2.5, most preferably from 1.9 to 2.5.

The nonionic cellulose ethers of the present invention are further substituted with one or more hydrophobic substituents, preferably with acyclic or cyclic, saturated or unsaturated, branched or linear hydrocarbon groups, such as an alkyl, alkylaryl or arylalkyl group having at least 8 carbon atoms, generally from 8 to 32 carbon atoms, preferably from 10 to 30 carbon atoms, more preferably from 12 to 24 carbon atoms, and most preferably from 12 to 18 carbon atoms. As used herein the terms "arylalkyl group" and "alkylaryl group" mean groups containing both aromatic and aliphatic structures. The most preferred aliphatic hydrophobic substituent is the hexadecyl group, which is most preferably straight-chained. The hydrophobic substituent is non-ionic.

The average number of moles of the hydrophobic substituent(s) per mole of anhydroglucose unit is designated as hydrophobe DS (hydrophobe degree of substitution). The DS is measured using the Morgan modification of the Zeisel method as described above, but using a gas chromatograph to measure the concentration of cleaved alkyl groups. An example of a gas chromatographic method that can be used for this purpose is described in ASTM method D-4794 (2009). In the case of alkylaryl hydrophobes such as dodecylphenyl glycidyl ether, the spectrophotometric method described in U.S. Pat. No. 6,372,901 issued Apr. 16, 2002 can be used to determine the hydrophobe DS. The hydrophobe DS is preferably at least 0.0003, more preferably at least 0.001, most preferably at least 0.003, and in particular at least 0.005 moles to 0.012 moles of the hydrophobic substituent(s), per mole of anhydroglucose unit. The average substitution level of the hydrophobic substituent(s) is generally up to 0.012, typically up to 0.010. The upper limit of hydrophobe substitution is determined by the water-solubility of the resulting nonionic cellulose ether. With increasing hydrophobe substitution, a point is reached at which the resulting polymer is water-insoluble. As noted in examples 49 and 50, for a hexadecyl group, the nonionic cellulose ether was rendered water-insoluble at a hydrophobe substitution of 0.015. This upper limit varies somewhat depending on the specific hydrophobe used and the method in which it is added. More than one type of hydrophobic substituent can be substituted onto the cellulose ether, but the total substitution level is preferably within the ranges set forth above.

The nonionic cellulose ethers of the present invention preferably have a weight average molecular weight of at least 1,000,000, more preferably at least 1,300,000. Their weight average molecular weight is preferably up to 2,500,000, more preferably up to 2,000,000. The weight average molecular weight is measured by size-exclusion chromatography (SEC) using the procedure described below.

The nonionic cellulose ethers of the present invention preferably have a Brookfield viscosity of at least 5000 mPa-sec, more preferably at least 6000 mPa-sec, and even more preferably at least 9000 mPa-sec. The nonionic cellulose ethers of the present invention preferably have a Brookfield viscosity of up to 20,000 mPa-sec, more preferably up to 18,000 mPa-sec, and most preferably up to 16,000 mPa-sec. The Brookfield viscosity is measured as 1% aqueous solution at 30 rpm, spindle #4 at 25.0° C. on a Brookfield viscometer. The Brookfield viscosity is dependent on the hydrophobe substitution, but is also an indication of the molecular weight of the nonionic cellulose ether.

The nonionic cellulose ether of the present invention has at least one of the properties further described below: a) a retained dynamic viscosity, % $\eta_{80/25}$, of at least 30 percent; b) a storage modulus of at least 15 Pascals at 25° C. and a retained storage modulus, % $G'_{80/25}$, of at least 12 percent; c) a critical association concentration of less than 15 ppm as measured by light-scattering.

Preferably, the nonionic cellulose ether of the present invention has two of the properties a), b) and c) in combination. More preferably the nonionic cellulose ether of the present invention has all three properties a), b) and c) in combination.

Most water-soluble polymers, including the nonionic cellulose ethers of this invention, are usually described as viscoelastic, which means that the flow properties of the polymer solutions exhibit components of both viscous and elastic flow. The viscous component is often characterized using the loss modulus which is related to the energy loss in the solution under shear stress, while the elastic component is often characterized using the storage modulus which is related to the energy stored in the solution under shear stress. In an oscillatory experiment, the retained dynamic viscosity is determined by dividing the loss modulus by the frequency of oscillation (in radians).

The retained dynamic viscosity % $\eta_{80/25}$ is preferably at least 35 percent, and more preferably at least 40 percent, wherein % $\eta_{80/25}$=[dynamic solution viscosity at 80° C./dynamic solution viscosity at 25° C.]×100, the dynamic solution viscosity at 25° C. and 80° C. being measured as 1% aqueous solution. The dynamic viscosity is measured at 25° C. and at 80° C. respectively using a TA Instruments AR-2000 oscillatory rheometer with a Couette geometry, a frequency of 0.5 Hertz, an applied stress of 0.1809 Pascals, and a heat-up ramp rate of 2° C./minute. It has been found that according to the present invention generally a retained dynamic viscosity % $\eta_{80/25}$ of up to 60 percent can be achieved.

The storage modulus is preferably at least 21 Pascals, more preferably at least 24 Pascals at 25° C. The retained storage modulus at 80° C. (% $G'_{80/25}$) is preferably at least 15 percent, more preferably at least 20 percent, wherein % $G'_{80/25}$=[storage modulus at 80° C./storage modulus at 25° C.]×100, the storage modulus at 25° C. and 80° C. being measured as a 1% aqueous solution. The storage modulus is measured at 25° C. and at 80° C. respectively using a TA Instruments AR-2000 oscillatory rheometer with a Couette geometry, a frequency of 0.5 Hertz, an applied stress of 0.1809 Pascals, and a heat-up ramp rate of 2° C./minute. It has been found that according to the present invention generally a storage modulus of up to 50 Pascals can be achieved. Also, generally a retained storage modulus % $G'_{80/25}$ of up to 30 percent can be achieved.

The critical association concentration is preferably less than 14 ppm. In the most preferred embodiments the critical association concentration of the nonionic cellulose ethers of the present invention can even be as low as 10 ppm.

The nonionic cellulose ether of the present invention can be produced in two ways:

According to a first method, hydroxyethyl cellulose is first reacted with an alkali metal hydroxide at a mole ratio of alkali metal hydroxide to cellulose of 0.20 to 1.5 and then with a hydrophobe-containing reagent. According to a second method, cellulose is reacted with alkali metal hydroxide at a mole ratio of alkali metal hydroxide to cellulose of 0.2 to 2.0 to prepare alkali cellulose, and the produced alkali cellulose is reacted with ethylene oxide and with a hydrophobe-containing reagent after adjusting the mole ratio of alkali metal hydroxide to cellulose of 0.1 to 1.0.

Many hydrophobe-containing reagents suitable for use as hydrophobic substituents are commercially available such as 1-bromododecane, 1-bromotetradecane, 1-bromohexadecane, 1-bromooctadecane, 1-bromoeicosane, and 1-bromodocosane. In addition, methods for preparing such hydrophobe-containing reagents, as well as methods for derivatizing cellulose ethers to comprise such hydrophobic substituents, are known to those skilled in the art (for example, U.S. Pat. No. 4,228,277 issued Oct. 14, 1980, U.S. Pat. No. 4,663,159 issued May 5, 1987, U.S. Pat. No. 4,845,175 issued Jul. 4, 1989, and U.S. Pat. No. 5,426,182 issued Jun. 20, 1995).

Preferred hydrophobic substituents include those derived from hydrophobe-containing reagents comprising acyclic or cyclic, saturated or unsaturated, branched or linear hydrocarbon groups having at least 8 carbon atoms, preferably those described further above. The hydrophobe-containing reagent can be attached to the hydroxyethyl cellulose via an ether, 2-hydroxypropoxyl, ester, or urethane linkage. Preferred is the ether linkage. Preferred hydrophobe-containing reagents hydrophobe sources are glycidyl ethers, such as nonylphenyl glycidyl ether, dodecylphenyl glycidyl ether, 3-n-pentadecenylphenyl glycidyl ether, hexadecyl glycidyl ether, octadecyl glycidyl ether, or docosyl glycidyl ether; or alpha-olefin epoxides, such as 1,2-epoxy hexadecane, 1,2-epoxyoctadecane, and their respective chlorohydrins; or alkyl halides, such as octyl bromide, decyl bromide, dodecyl bromide, tetradecyl bromide, hexadecyl bromide, octadecyl bromide, eicosyl bromide; and mixtures thereof.

After completion of the reaction according to the first or second method, the reaction mixture can be processed in a known manner, such as neutralization of residual alkali with a suitable acid such as acetic acid, formic acid, hydrochloric acid, nitric acid, or phosphoric acid, recovering the product, washing it with an inert diluent to remove unwanted by-products, and drying the product.

In one embodiment, the personal care composition further comprises one or more rheology modifier polymers such as, for example, Acrylates Steareth-20 Methacrylate Copolymer, Acrylates Beheneth-25 Methacrylate Copolymer, Acrylates Steareth-20 Methacrylate Crosspolymer, Acrylates Copolymer, Acrylates/Vinylneodecanoate Crosspolymer, and mixtures thereof.

In one embodiment, the personal care composition, is heat stable up to at least 60° C.

In one embodiment, the personal care composition is a hair care composition. In such embodiments, the nonionic cellulose ether is present in a range from 0.1 wt % to 10 wt % by weight of the personal care composition, preferably in a range from 0.5 wt % to 5 wt %.

In one embodiment, the hair care composition is a hair fixative. In one embodiment, the hair fixative polymer is at least one of PVP/VA copolymer, ethyl ester of PVM/MA copolymer, butyl ester of PVM/MA copolymer, vinyl acetate/crotonic acid copolymer, vinyl acetate/crotonic acid/vinyl neodecanoate, VA/butyl maleate/isobornyl acrylate copolymer, acrylates copolymer, diglycol/CHDM/isophthalates/SIP copolymer, acrylates/hydroxyester acrylates copolymer, methacrylates/acrylates copolymer/amine salt, AMP-acrylates/diacetone-acrylamide copolymer, AMPD-acrylates/diacetone-acrylamide copolymer, acrylates/methacrylate polymers, acrylates/acrylamide copolymer, PVP/vinyl caprolactam/DMAPA acrylates copolymer, polyvinylcaprolactam, isobutylene/ethylmaleimide/hydroxyethylmaleimide copolymer, acrylates/succinates/hydroxyacrylates copolymer, polyurethane-1, Octylacrylamide/Acrylates/Butylaminoethyl Methacrylate Copolymer, Vinyl caprolactam/VP/Dimethylaminoethyl Methacrylate Copolymer, Acrylates/t-Butylacrylamide Copolymer, Acrylates/C1-2 Succinates/Hydroxyacrylates Copolymer, Acrylamide/Sodium Acryloyldimethyltaurate/Acrylic Acid Polymer and mixtures thereof.

In one embodiment, the personal care composition is a skin care composition. In such embodiments, the nonionic cellulose ether is present in a range from 0.1 wt % to 10 wt % by weight of the personal care composition, preferably in a range from 0.5 wt % to 5 wt %. In one embodiment, the personal care composition contains an antioxidant, anti-aging active, or sun care active.

Regardless of whether a hair care or skin care composition, in a preferred embodiment, the personal care composition is formulated as an emulsion, gel or other aqueous based formulation, to enable a stable, airy, whipped texture at room temperature, preferentially displaying structural stability over a broad range of high temperature exposure. Personal care products of the present invention exhibit a texture that can be described as airy, whipped, fluffy, and/or light. As can be appreciated, the texture of personal care formulations can have a major influence on consumer perception of product performance. For example, products with an airy, light texture will be perceived by consumers to improve hair volume or result in faster absorbance into skin. Moreover, personal care products of the present invention exhibit marked ability to maintain their airy, light emulsion structure during product transportation and shelf-life storage.

In some embodiments, the personal care composition includes an emollient. The emollient may be at least one of moisturizer, conditioner, oil, or other fatty substance. For example, when the composition is in an emulsion form, it comprises at least one oily phase that contains at least one oil, especially a cosmetically acceptable oil. The term "oil" means a fatty substance that is liquid at room temperature.

Examples of oils include hydrocarbon-based oils of animal origin, such as squalene, hydrocarbon-based oils of plant origin, such as liquid triglycerides of fatty acids comprising from 4 to 10 carbon atoms, for instance heptanoic or octanoic acid triglycerides, or alternatively, oils of plant origin, for example sunflower oil, corn oil, soybean oil, marrow oil, grapeseed oil, sesame seed oil, hazelnut oil, apricot oil, macadamia oil, arara oil, coriander oil, castor oil, avocado oil, jojoba oil, shea butter oil, or caprylic/capric acid triglycerides, MIGLYOL 810, 812 and 818 (from Dynamit Nobel), synthetic esters and ethers, especially of fatty acids, for instance the oils of formulae $R^1COOR^2$ and $R^1OR^2$ in which $R^1$ represents a fatty acid residue comprising from 8 to 29 carbon atoms and $R^2$ represents a branched or unbranched hydrocarbon-based chain comprising from 3 to 30 carbon atoms, for instance purcellin oil, isononyl isononanoate, isopropyl myristate, 2-ethylhexyl palmitate, 2-octyldodecyl stearate, 2-octyldodecyl erucate or isostearyl isostearate, hydroxylated esters, for instance isostearyl lactate, octyl hydroxystearate, octyldodecyl hydroxystearate, diisostearyl malate, triisocetyl citrate and fatty alcohol heptanoates, octanoates and decanoates, polyol esters, for instance propylene glycol dioctanoate, neopentyl glycol diheptanoate and diethylene glycol diisononanoate, pentaerythritol esters, for instance pentaerythrityl tetraisostearate, lipophilic derivatives of amino acids, such as isopropyl lauroyl sarcosinate, such as is sold under the name ELDEW SL 205 (from Ajinomoto), linear or branched hydrocarbons of mineral or synthetic origin, such as mineral oils (mixtures of petroleum-derived hydrocarbon-based oils), volatile or non-volatile liquid paraffins, and derivatives thereof, petroleum jelly, polydecenes, isohexadecane, isododecane, hydrogenated isoparaffin (or polyisobutene), silicone oils, for instance volatile or non-volatile polymethylsiloxanes (PDMS) comprising a linear or cyclic silicone chain, which are liquid or pasty at room temperature, especially cyclopolydimethylsiloxanes (cyclomethicones) such as cyclopentasiloxane and cyclohexadimethylsiloxane, polydimethylsiloxanes comprising alkyl, alkoxy or phenyl groups, which are pendent or at the end of a silicone chain, these groups comprising from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes 2-phenylethyltrimethyl siloxysilicates and polymethylphenylsiloxanes, fluoro oils such as partially hydrocarbon-based and/or partially silicone-based fluoro oils, ethers such as dicaprylyl ether (CTFA name: dicaprylyl ether), and $C_{12}$-$C_{15}$ fatty alcohol benzoates (FINSOLV TN from Finetex), mixtures thereof.

Oils include mineral oil, lanolin oil, coconut oil and derivatives thereof, cocoa butter, olive oil, almond oil, macadamia nut oil, *aloe* extracts such as *aloe vera* lipoquinone, jojoba oils, safflower oil, corn oil, liquid lanolin, cottonseed oil, peanut oil, hydrogenated vegetable oil, squalane, castor oil, polybutene, sweet almond oil, avocado oil, calophyllum oil, ricin oil, vitamin E acetate, olive oil, silicone oils such as dimethylopolysiloxane and cyclomethicone, linolenic alcohol, oleyl alcohol, and the oil of cereal germs.

Other suitable emollients include dicaprylyl ether, $C_{12-15}$ alkyl benzoate, DC 200 FLUID 350 silicone fluid (from Dow Corning Corp.), isopropyl palmitate, octyl palmitate, isopropyl myristate, hexadecyl stearate, butyl stearate, decyl oleate, acetyl glycerides, the octanoates and benzoates of $C_{12-15}$ alcohols, the octanoates and decanoates of alcohols and polyalcohols such as those of glycol and glyceryl, ricinoleates esters such as isopropyl adipate, hexyl laurate and octyl dodecanoate, dicaprylyl maleate, phenyltrimethicone, and *aloe vera* extract. Solid or semi-solid cosmetic emollients include glyceryl dilaurate, hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate.

In one embodiment, the emollient is present in an amount from 0.05% to 40% by weight of the composition. Preferably, the emollient is present in an amount from 0.1% to 10% by weight of the composition.

In some embodiments, the personal care composition includes an emulsifier or a surfactant. Suitable emulsifiers are selected from amphoteric, anionic, cationic and nonionic emulsifiers, used alone or as a mixture. Anionic surfactants include soaps or salts of fatty acids, alkyl sulfates, alkyl ether sulfates, alpha-olefin sulfonates, alkyl aryl sulfonates, sarcosinates, alkyl glucose esters or their alkoxylates, and in particular sodium lauryl sulfate, ammonium lauryl sulfate, triethanolamine lauryl sulfate, sodium laureth sulfate, isethionates, and triethanolamine stearate. Nonionic surfactants include methyl glucose stearates or their ethoxylates, alkyl polyglucosides, and glycerol monostearate, fatty acid alkanol amides, alkyl aryl polyglycol ether, polyglycol ethers and in particular cocoyl diethanolamide, nonoxynol-7 and octoxynol-9; cationics including alkyl trimethyl ammonium salts, quaternized amides of ethylene diamine, alkyl pyridinium salts and in particular cetrimonium chloride, stearalkonium chloride and cetyl pyridinium chloride; and amphoterics including alkyl .beta.-aminopropionates, betaines, alkyl imidazolines and in particular cocamidopropyl betaine and caproam phocarboxy propionate. Polymeric cationic emulsifiers that include hydrophobic moieties are preferred, examples of which include polyquaternium-24 and polyquaternium 67 (SOFTCAT™), available from The Dow Chemical Company.

Emulsions free of emulsifying surfactants or comprising less than 0.5% of emulsifying surfactants relative to the total weight of the composition may also be prepared, by using suitable compounds, for example polymers having emulsifying properties, such as CARBOPOL 1342 polymer (Noveon), PEMULEN polymer (Noveon), SEPIGEL 305 polyacrylamide/C13-C14 isoparaffin/laureth-7 (Seppic), particles of ionic or nonionic polymers, particles of anionic polymer such as, isophthalic acid, sulfoisophthalic acid polymers, and phthalate/sulfoisophthalate/glycol copolymers (for example diethylene glycol/phthalate/isophthalate/1,4-cyclohexanedimethanol sold under the names Eastman AQ diglycol/CHDM/isophthalates/SIP copolymer (AQ35S, AQ38S, AQ55S and/or AQ48 Ultra, from Eastman Chemical). Emulsifier-free emulsions stabilized with silicone particles or metal oxide particles such as $TiO_2$ or the like may also be prepared.

The emulsifier or surfactant may be present in an amount from 0.01% to 15% by weight of the composition. In one embodiment, the surfactant is present in an amount from 0.1% to 5% by weight of the composition.

In some embodiments, the personal care composition includes a thickener. Examples of thickeners include polymers, for example, modified or unmodified carboxyvinyl polymers, such as the products sold under the names CARBOPOL and PEMULEN (INCI name: Acrylates/C10-30 alkyl acrylate crosspolymer; available from Noveon), polyacrylates and polymethacrylates, such as the products sold under the names LUBRAJEL and NORGEL (from Guardian) or HISPAGEL (from Hispano Chimica), polyacrylamides, 2-acrylamido-2-methylpropanesulfonic acid polymers and copolymers, which are optionally crosslinked and/or neutralized, for instance the poly(2-acrylamido-2-methylpropane-sulfonic acid) sold by Clariant (INCI name: ammonium polyacryldimethyltauramide), emulsified crosslinked anionic copolymers of acrylamide and AMPS, such as those sold under the name SEPIGEL 305 (INCI name: Polyacrylamide/C13-14 Isoparaffin/Laureth-7; from Seppic) and under the name SIMULGEL 600 (INCI name: Acrylamide/Sodium acryloyldimethyltaurate copolymer/Isohexadecane/Polysorbate 80; from Seppic), polysaccharide biopolymers, for instance xanthan gum, guar gum, carob gum, acacia gum, scleroglucans, chitin and chitosan derivatives, carrageenans, gellans, alginates, celluloses such as microcrystalline cellulose, carboxymethylcellulose, hydroxymethylcellulose and hydroxypropylcellulose, associative polymers, for instance associative polyurethanes, copolymers comprising at least two hydrocarbon-based lipophilic chains comprising from 6 to 30 carbon atoms, separated with a hydrophilic sequence, such as the polyurethanes sold under the names SERAD FX1010, SERAD FX1100 and SERAD FX1035 (from Hüls America), RHEOLATE 255, RHEOLATE 278 and RHEOLATE 244 (INCI name: Polyetherurea-polyurethane; from Rheox), DW 1206F, DW 1206J, DW 1206B, DW 1206G, and ACRYSOL RM 2020 (from Röhm & Haas), ACULYN 44, ACULYN 46 (from The Dow Chemical Company), or sodium magnesium silicate, for instance LAPONITE XLG. One preferred thickener is METHOCEL hydroxypropyl methylcellulose, available from The Dow Chemical Company.

In one embodiment, the thickener is present in an amount from 0.01% to 10% by weight of the composition. In one embodiment, the thickener is present in an amount from 0.1% to 5% by weight of the composition.

The personal care composition also comprises a suitable carrier, or mixtures of carriers. The type of carrier depends on the particular end use of the composition. Illustrative carriers include, for example, water, such as deionized or distilled water, emulsions, such as oil-in-water or water-in-oil emulsions, alcohols, such as ethanol, isopropanol or the like, glycols, such as propylene glycol, glycerine or the like, or combinations thereof. A preferred carrier is deionized water.

In one embodiment, the personal care compositions of the present invention further comprise an active ingredient selected from skin care actives, nail care actives, or hair care actives. Actives include sunscreens, skin colorants, drug substances (such as anti-inflammatory agents, antibiotics, topical anesthetics, antimycotics, keratolytics, and the like), skin protectants, conditioners, humectants, and ultraviolet radiation absorbers.

Examples of sunscreens include para aminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, trolamine salicylate, titanium dioxide, zinc oxide, benzophenones, benzylidenes, salicylates, or other known UV filters, including diethanolamine methoxycinnamate, digalloy trioleate, ethyl dihydroxypropyl PABA, glyceryl aminobenzoate, and lawsone with dihydroxy acetone and red petrolatum.

In one embodiment, the personal care compositions of the present invention further comprise at least one additional ingredient. Optional ingredients include any suitable substance for personal care compositions, for example, colorants, preservatives, pH adjustors, reducing agents, fragrances, foaming agents, tanning agents, depilatory agents, astringents, antiseptics, deodorants, antiperspirants, insect repellants, and biocides.

Colorants include pigments, which are used especially in make-up, including metal oxide pigments, titanium dioxide, optionally surface-treated, zirconium oxide or cerium oxide, zinc oxide, iron oxide (black, yellow or red), chromium oxide, manganese violet, ultramarine blue, chromium hydrate and ferric blue, carbon black, pigments of barium, strontium, calcium or aluminum (for example D & C or FD & C), cochineal carmine, mica coated with titanium or with bismuth oxychloride, titanium mica with iron oxides, titanium mica with, especially, ferric blue or chromium oxide, titanium mica with an organic pigment, nacreous pigments based on bismuth oxychloride, goniochromatic pigments, for example pigments with a multilayer interference structure, reflective pigments, for example particles with a silver-coated glass substrate, glass substrate coated with nickel/chromium/ molybdenum alloy, glass substrate coated with brown iron oxide, particles comprising a stack of at least two polymer layers, for instance MIRROR GLITTER (from 3M).

Dyes include water-soluble dyes such as copper sulfate, iron sulfate, water-soluble sulfopolyesters, rhodamines, natural dyes, for instance carotene and beetroot juice, methylene blue, caramel, the disodium salt of tartrazine and the disodium salt of fuschin, and mixtures thereof. Liposoluble dyes may also optionally be used.

Preservatives include alcohols, aldehydes, methylchloroisothiazolinone and methylisothiazolinone, p-hydroxybenzoates, and in particular methylparaben, propylparaben, glutaraldehyde and ethyl alcohol.

The pH adjustors, include inorganic and organic acids and bases and in particular aqueous ammonia, citric acid, phosphoric acid, acetic acid, sodium hydroxide, potassium hydroxide, and triethanolamine. In a preferred embodiment, the pH adjustor is aminomethyl propanol, L-arginine, tromethamine, PEG-15 cocamine, diisopropanolamine, triisopropanolamine, or tetrahydroxypropyl ethylenediamine. In a particularly preferred embodiment, the pH adjustor is amino methyl propanol, Aminomethyl propanol is available under the tradename AMP-ULTRA from Angus Chemical Company. In one embodiment, the pH adjustor is present in an amount from 0.01% to 1% by weight of the composition. In one embodiment, the pH adjustor is present in an amount from 0.1% to 0.5% by weight of the composition.

Reducing agents include ammonium thioglycolate, hydroquinone and sodium thioglycolate.

Fragrances include any component which provides a pleasant scent. Fragrances are generally aldehydes or ketones, and often oils obtained by extraction of natural substances or synthetically produced. Often, fragrances are accompanied by auxiliary materials, such as fixatives, extenders, stabilizers and solvents.

Biocides include antimicrobials, bactericides, fungicides, algaecides, mildicides, disinfectants, antiseptics, and insecticides.

The amount of optional ingredients effective for achieving the desired property provided by such ingredients can be readily determined by one skilled in the art.

In one embodiment, the personal care composition may be formulated in the form of a leave-on hair composition, containing a moisturizer, conditioner, and/or styling active. In one embodiment, the personal care composition may be formulated in the form of a skin care composition, such as a lotion or cream, containing a moisturizer, anti-aging, and/or suncare active.

EXAMPLES

The following examples are for illustrative purposes only and are not intended to limit the scope of the present invention. All percentages are by weight unless otherwise specified.

Example 1

An example of a personal care composition of the present invention is listed in TABLE 1, in wt %:

TABLE 1

|   |   | Batch A |
|---|---|---|
| A | DI water | 69.3 |
|   | Hydrophobically-modified Hydroxyethyl Cellulose | 0.5 |
|   | Acrylates/Hydroxyester acrylates copolymer (40% solids) | 4.0 |
| B | DI water | 20.0 |
|   | Acrylate/Steareth-20 Methacrylate Crosspolymer (29% solids) | 2.0 |
| C | Stepan Stearyl Alcohol | 1.0 |
|   | Stepan Cetyl Alcohol | 2.0 |
|   | PEG-40 hydrogenated castor oil | 0.1 |
| D | Aminomethyl proponal | 0.4 |
| E | Propylene Glycol | 0.2 |
|   | Vitamin E acetate USP | 0.01 |
|   | Methylisothiazolinone, Phenoxyethanol | 0.45 |

To prepare the formulation, the DI water from Part A is heated to 70-75° C., and the remaining Part A components are sprinkled in and stirred. The Part B components are then added to Part A and mixed, while maintaining the temperature.

The Part C components are combined in a separate vessel, and heated slowly to liquefy at 70-75° C. The Part C phase is then slowing added to the Part A & B mixture, and mixed at high speed for 5 minutes while maintaining the temperature. The heat is then removed, and Part D added before the formulation cools.

The resulting formulation is allowed to air cool to 40° C., and Part E is added, and the formulation mixed for 15 minutes.

Example 2

Comparative

An example of a comparative personal care composition is listed in TABLE 2, in wt %:

TABLE 2

|   |   | Comparative Batch 1 |
|---|---|---|
| A | DI water | 69.3 |
|   | CELLOSIZE PCG-10 Hydroxyethyl Cellulose | 0.5 |
|   | Acrylates/Hydroxyester acrylates copolymer (40% solids) | 4.0 |
| B | DI water | 20.0 |
|   | Acrylate/Steareth-20 Methacrylate Crosspolymer (29% solids) | 2.0 |
| C | Stepan Stearyl Alcohol | 1.0 |
|   | Stepan Cetyl Alcohol | 2.0 |
|   | PEG-40 hydrogenated castor oil | 0.1 |

TABLE 2-continued

|   |   | Comparative Batch 1 |
|---|---|---|
| D | Aminomethyl proponal | 0.4 |
| E | Propylene Glycol | 0.2 |
|   | Vitamin E acetate USP | 0.01 |
|   | Methylisothiazolinone, Phenoxyethanol | 0.45 |

The formulation is prepared substantially similar to Example 1.

Example 3

Examples of personal care compositions of the present invention are listed in TABLE 3, in wt %:

TABLE 3

|   |   | Batch B | Batch C |
|---|---|---|---|
| A | DI water | 61.7 | 61.2 |
|   | Hydrophobically-modified Hydroxyethyl Cellulose | 0.5 | 0.5 |
|   | Low Gelation Temperature Methyl Cellulose | — | 0.5 |
|   | Acrylates/Hydroxyester acrylates copolymer (45% solids) | 4.0 | 4.0 |
| B | DI water | 20.0 | 20.0 |
|   | Sodium Magnesium Silicate | 0.1 | 0.1 |
|   | Acrylate/Steareth-20 Methacrylate Crosspolymer (29% solids) | 2.0 | 2.0 |
| C | Cocoamido betaine | 0.5 | 0.5 |
|   | Cetearyl Isononanoate, Ceteareth-20, Cetearyl Alcohol, Glyceryl Stearate, Glycerin, Ceteareth-12, Cetyl Palmitate | 5.0 | 5.0 |
|   | Pentaerythrityl Tetracaprylate/Tetracaprate | 5.0 | 5.0 |
|   | PEG-40 hydrogenated castor oil | 0.1 | 0.1 |
| D | AMP-95 Aminomethyl proponal | 0.4 | 0.4 |
| E | Propylene Glycol | 0.2 | 0.2 |
|   | Methylisothiazolinone, Phenoxyethanol | 0.45 | 0.45 |

The formulations are prepared substantially similar to Example 1. Low Gelation Temperature Methyl Cellulose refers to a grade of methylcellulose that gels at a relatively low temperature, 38° C. to 44° C., is generally available under the tradename METHOCEL SG or SGA (The Dow Chemical Company). No grades of commercially available methylcellulose gel at temperatures as low as an individual's normal body temperature, however, U.S. Pat. No. 6,235,893, the entirety of which is incorporated by reference herein, teaches methylcelluloses that gel as low as 31° C.

Example 4

To test aesthetic desirability, Batches A & B, and Comparative Batch 1 from the previous examples were made. Upon evaluation by a trained panelist, Batch A was characterized as an "airy, gel-like lotion," Batch B was characterized as an "airy lotion," whereas Comparative Batch 1 was characterized as a "very elastic gel," which is aesthetically unacceptable. CELLOSIZE Hydroxyethyl Cellulose is a known thickener; accordingly, the exemplary texture of the inventive samples cannot be attributed to mere thickening ability.

Batch B was tested conventionally and showed good heat aging stability with no phase separation, maintaining a fluffy, airy lotion texture after a 10 day, 60° C. heat aging stability test. The formulation was stored in a clear glass jar, sealed with plastic screw cap. The glass container was then stored in 60° C. oven for 10 days. At the end of the testing cycle, the sample was equilibrated at room temperature. Visual observation on formulation appearance and phase separation was made by a trained panelist to determine formulation heat-aging stability.

The invention claimed is:

1. A personal care composition, comprising:
   water;
   a hydroxyethyl cellulose substituted with at least one hydrophobic substituent selected from the group consisting of nonylphenyl glycidl ether, 3-n-pentadecenylphenyl glycidyl ether, hexadecyl glycidyl ether, octadecyl glycidyl ether, docosyl glycidyl ether, 1,2-epoxyhexadecane, 1,2-epoxyoctadecane and $C_{8-32}$ alkyl halide wherein the substituted hydroxyethyl cellulose has a weight average molecular weight of from 1,000,000 to 2,500,000; and
   at least one hair fixative polymer, moisturizer, conditioner, humectant, cationic conditioning polymer, antioxidant, anti-aging active, or sun care active.

2. The personal care composition of claim 1, wherein the personal care composition is a hair care composition.

3. The personal care composition of claim 1, wherein the substituted hydroxyethyl cellulose is present in a range from 0.1 wt % to 10 wt % by weight of the personal care composition.

4. The personal care composition of claim 1, wherein the hair fixative polymer is at least one of VP/PA copolymer, ethyl ester of VM/MA copolymer, butyl ester of VM/MA copolymer, vinyl acetate/crotonic acid copolymer, vinyl acetate/crotonic acid/vinyl neodecanoate, VA/butyl maleate/isobornyl acrylate copolymer, acrylates copolymer, diglycol/CHDM/isophthalates/SIP copolymer, acrylates/hydroxyester acrylates copolymer, methacrylates/acrylates copolymer/amine salt, AMP-acrylates/diacetone-acrylamide copolymer, AMPD-acrylates/diacetone-acrylamide copolymer, acrylates/methacrylate polymers, acrylates/acrylamide copolymer, VP/vinyl caprolactam/DMAPA acrylates copolymer, polyvinylcaprolactam, isobutylene/ethylmaleimide/hydroxyethylmaleimide copolymer, acrylates/succinates/hydroxyacrylates copolymer, polyurethane-1, Octylacrylamide/Acrylates/Butylaminoethyl Methacrylate Copolymer, Vinyl caprolactam/VP/Dimethylaminoethyl Methacrylate Copolymer, Acrylates/t-Butylacrylamide Copolymer, Acrylates/C1-2 Succinates/Hydroxyacrylates Copolymer, Acrylamide/Sodium Acryloyldimethyltaurate/Acrylic Acid Polymer and mixtures thereof.

5. The personal care composition of claim 1, further comprising one or more rheology modifier polymers.

6. The personal care composition of claim 1, wherein the personal care composition is heat stable up to at least 60° C.

7. The personal care composition of claim 1, wherein the personal care composition is a skin care composition.

8. The personal care composition of claim 7, wherein the substituted hydroxyethyl cellulose is present in a range from 0.1 wt % to 10 wt % by weight of the personal care composition.

9. The personal care composition of claim 7, wherein the personal care composition contains an antioxidant, anti-aging active, or sun care active.

10. A method for stabilizing a personal care composition against heat collapse, comprising:
    incorporating into the personal care composition a hydroxyethyl cellulose substituted with at least one hydrophobic substituent selected from the group consisting of nonylphenyl glycidyl ether, 3-n-pentadecenylphenyl glycidyl ether, hexadecyl glycidyl ether, octadecyl glycidyl ether, docosyl glycidyl ether, 1,2- epoxy hexadecane, 1,2-epoxyoctadecane and $C_{8-32}$ alkyl halide wherein the substituted hydroxyethyl cellulose has a weight average molecular weight of from 1,000,000 to 2,500,000.

11. The personal care composition of claim 3, wherein the substituted hydroxyethyl cellulose is present in a range from 0.5 wt % to 5 wt % by weight of the personal care composition.

12. The personal care composition of claim 5, wherein the one or more rheology modifier polymers are selected from the group consisting of Acrylates Steareth-20 Methacrylate Copolymer, Acrylates Beheneth-25 Methacrylate Copolymer, Acrylates Steareth-20 Methacrylate Crosspolymer, Acrylates Copolymer, Acrylates/Vinylneodecanoate Crosspolymer, and mixtures thereof.

13. The personal care composition of claim 8, wherein the substituted hydroxyethyl cellulose is present in a range from 0.5 wt % to 5 wt % by weight of the personal care composition.

14. The personal care composition of claim 1, wherein the alkyl halide is selected from the group consisting of octyl bromide, decyl bromide, dodecyl bromide, tetradecyl bromide, hexadecyl bromide, octadecyl bromide and eicosyl bromide.

15. The method of claim 10, wherein the alkyl halide is selected from the group consisting of octyl bromide, decyl bromide, dodecyl bromide, tetradecyl bromide, hexadecyl bromide, octadecyl bromide and eicosyl bromide.

* * * * *